United States Patent
Masumura et al.

(10) Patent No.: US 10,859,483 B2
(45) Date of Patent: Dec. 8, 2020

(54) AUTOMATIC ANALYSIS APPARATUS, AUTOMATIC ANALYSIS METHOD, AND STORAGE MEDIUM

(71) Applicants: CANON KABUSHIKI KAISHA, Tokyo (JP); CANON MEDICAL SYSTEMS CORPORATION, Otawara (JP)

(72) Inventors: Takahiro Masumura, Utsunomiya (JP); Hirotoshi Tahara, Otawara (JP); Satoru Sugita, Otawara (JP)

(73) Assignees: CANON KABUSHIKI KAISHA, Tokyo (JP); CANON MEDICAL SYSTEMS CORPORATION, Otawara (JP)

(*) Notice: Subject to any disclaimer, the term of this patent is extended or adjusted under 35 U.S.C. 154(b) by 0 days.

(21) Appl. No.: 16/524,557

(22) Filed: Jul. 29, 2019

(65) Prior Publication Data
US 2020/0049606 A1 Feb. 13, 2020

(30) Foreign Application Priority Data

Aug. 7, 2018 (JP) .................... 2018-148340

(51) Int. Cl.
*G01N 21/21* (2006.01)
*G01N 15/02* (2006.01)
(Continued)

(52) U.S. Cl.
CPC ..... *G01N 15/0211* (2013.01); *G01N 15/0227* (2013.01); *G01N 21/21* (2013.01);
(Continued)

(58) Field of Classification Search
CPC .......... G01N 15/0211; G01N 15/0227; G01N 21/21; G01N 21/51; G01N 33/5005; G01N 2015/0222; G01N 2021/516
(Continued)

(56) References Cited

U.S. PATENT DOCUMENTS

| 9,023,282 | B2 | 5/2015 | Adachi et al. | |
| 2011/0299066 | A1* | 12/2011 | Kusukame | G01N 21/49 356/51 |
| 2015/0064742 | A1* | 3/2015 | Sakamoto | G01N 33/5005 435/34 |

FOREIGN PATENT DOCUMENTS

| JP | S62059841 A | 3/1987 |
| JP | 2007225348 A | 9/2007 |
| JP | 2015007649 A | 1/2015 |

OTHER PUBLICATIONS

Xu. "Electric field Monte Carlo simulation of polarized light propagation in turbid media." Optics Express. Dec. 27, 2004:6530-6539. vol. 12, No. 26. Cited in the specification.

* cited by examiner

*Primary Examiner* — Roy M Punnoose
(74) *Attorney, Agent, or Firm* — Rossi, Kimms & McDowell LLP

(57) ABSTRACT

An automatic analysis apparatus includes a reaction vessel configured to contain a reaction liquid in which a measuring object and a reagent are mixed with each other, an irradiation unit configured to irradiate the reaction vessel with irradiation light as predetermined incident light polarization, a measurement unit configured to measure light emitted from the reaction vessel, and a processor configured to process a signal having a specific polarization component obtained from the measurement unit and to analyze the measuring (Continued)

object. The specific polarization component is determined based on the condition of the reaction liquid.

27 Claims, 13 Drawing Sheets

(51) Int. Cl.
*G01N 21/51* (2006.01)
*G01N 33/50* (2006.01)

(52) U.S. Cl.
CPC ......... *G01N 21/51* (2013.01); *G01N 33/5005* (2013.01); *G01N 2015/0222* (2013.01); *G01N 2021/516* (2013.01)

(58) Field of Classification Search
USPC .......................................................... 356/369
See application file for complete search history.

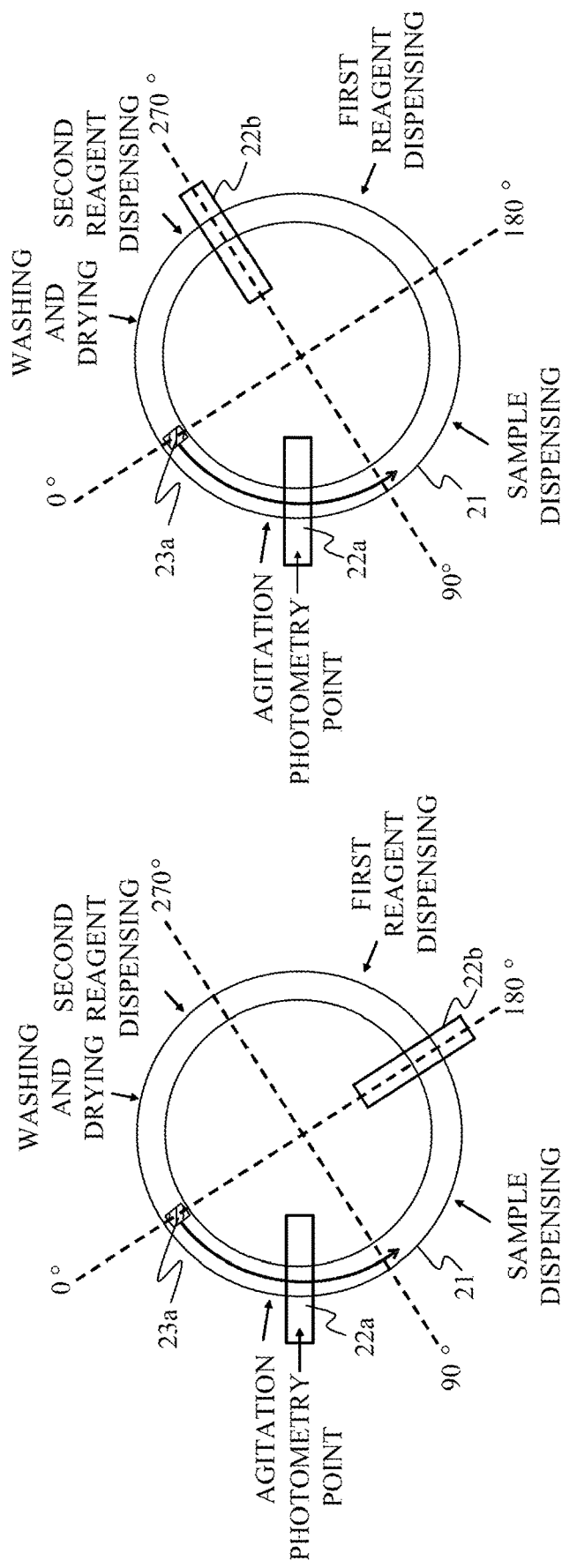

AUTOMATIC ANALYSIS APPARATUS, AUTOMATIC ANALYSIS METHOD, AND STORAGE MEDIUM

BACKGROUND OF THE INVENTION

Field of the Invention

The present invention relates to an automatic analysis apparatus that analyzes a component of a test object utilizing the latex aggregation reaction.

Description of the Related Art

The automatic analysis apparatus utilizing the latex aggregation reaction can highly sensitively quantify the test object (measuring object) when an optical signal change is larger, such as the intensity of scattered light or transmitted light, corresponding to the aggregate change (aggregate size, aggregate concentration) caused by the aggregation reaction. Japanese Patent Laid-Open No. ("JP") 2015-7649 discloses an automatic analysis apparatus that measures a scattered light intensity at a specific scattering angle. JP 62-59841 discloses a measurement method for measuring an aggregation reaction (immune reaction) using the polarization by addressing the anisotropy of the aggregate. The measurement method disclosed in JP 62-59841 detects a change in the aggregation state as a change in the polarization state, and thus can selectively measure the scattered light in which the polarization state has changed. This configuration can eliminate a noise component, such as unnecessary non-scattered light and scattered light having no change in polarization state, and measure the scattered light caused by the aggregation reaction with a relatively high sensitivity.

However, the automatic analysis apparatus disclosed in JP 2015-7649 has a different optimal angle for measuring an aggregate change with a high sensitivity according to the condition of the reaction liquid, such as the sizes and concentrations of the measuring object and latex particles and the aggregation state. It is thus necessary to change the angle (scattering angle) of the detector relative to the optical axis according to the condition of the reaction liquid, or to previously dispose a plurality of detectors corresponding to the scattering angles in order to handle a plurality of angles. As a result, the automatic analysis apparatus may have a complex configuration.

On the other hand, the measurement method disclosed in JP 62-59841 has difficulties in measuring the polarization change caused by the shape (anisotropy) of a single scatterer in the latex aggregation reaction. In addition, the condition for the highly sensitive measurement using the polarization is different according to the condition of the reaction liquid, such as the particle size and concentration of the latex particle, and the aggregation state.

SUMMARY OF THE INVENTION

The present invention provides a highly sensitive automatic analysis apparatus, an automatic analysis method, and a storage medium with a simple configuration.

An automatic analysis apparatus according to one aspect of the present invention includes a reaction vessel configured to contain a reaction liquid in which a measuring object and a reagent are mixed with each other, an irradiation unit configured to irradiate the reaction vessel with irradiation light as predetermined incident light polarization, a measurement unit configured to measure light emitted from the reaction vessel, and a processor configured to process a signal having a specific polarization component obtained from the measurement unit and to analyze the measuring object. The specific polarization component is determined based on the condition of the reaction liquid.

An automatic analysis method according to another aspect of the present invention includes the steps of irradiating a reaction vessel configured to contain a reaction liquid in which a measuring object and a reagent are mixed with each other, with irradiation light as predetermined incident light polarization, measuring light emitted from the reaction vessel, and processing a signal having a specific polarization component obtained from the measurement unit and to analyze the measuring object. The specific polarization component is determined based on the condition of the reaction liquid. A non-transitory computer-readable storage medium storing a program that causes a computer to execute the above automatic analysis method also constitutes another aspect of the present invention.

Further features of the present invention will become apparent from the following description of exemplary embodiments with reference to the attached drawings.

BRIEF DESCRIPTION OF THE DRAWINGS

FIGS. 14A to 14D illustrate another arrangement of the transmitted light measurement unit and the scattered light measurement unit according to the third embodiment.

DESCRIPTION OF THE EMBODIMENTS

Figure 1B:
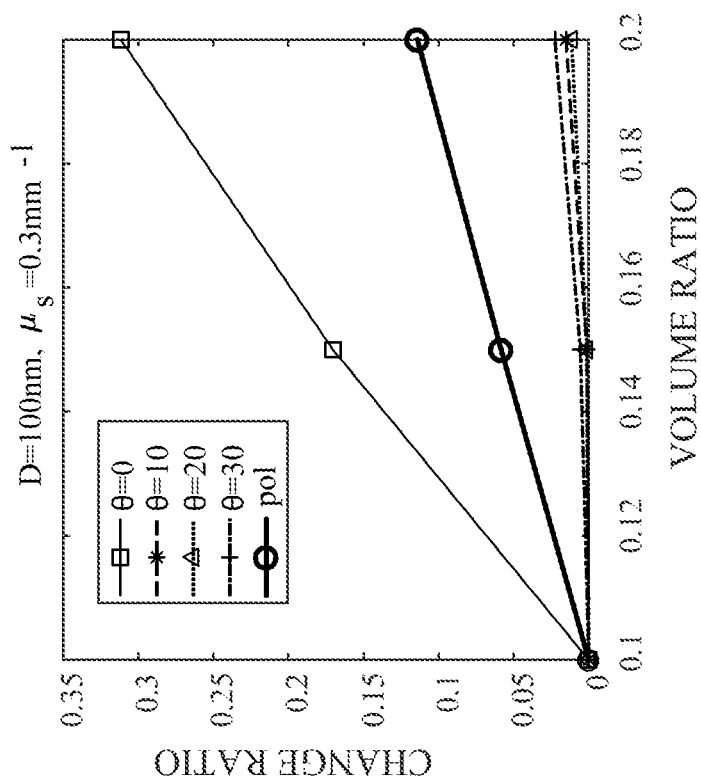
FIGS. 1A and 1B are simulation results of an effect according to this embodiment.

Referring now to the accompanying drawings, a detailed description will be given of embodiments according to the present invention.

(Principle of Automatic Analysis Apparatus)

An automatic analysis apparatus according to this embodiment mixes a reagent with a test sample, such as blood or urine, collected from a sample such as human, and measures a component amount (concentration) of a desired test item (measuring object) contained in the test sample. In the immune serum test item as one of the test items, the turbidimetric measurement method for measuring the turbidity change in the test sample is known and in particular, the analysis method using the latex aggregation reaction is used. This method quantifies the concentration of the measuring object by measuring the aggregate of latex particles. When the antigen (measuring object) contained in the test sample and the reagent containing a latex particle whose surface is modified with the antibody are mixed with each other, the antibody on the surface of the latex particle and the antigen react, and the latex particles clump via the antigen, and an aggregate of the latex particles is formed.

The automatic analysis apparatus according to this embodiment introduces light of a predetermined polarization state into a reaction liquid obtained by mixing a measuring object and a reagent containing latex particles with each other, selectively detects light of a specific polarization state among light emitted through a scattering process in the reaction liquid, and processes and analyzes the detected light. For example, this embodiment removes (or reduces) a noise component, such as non-scattered light, by selectively detecting light whose polarization state has changed from the polarization state in the incident state, and measures the latex aggregation change with a relatively high sensitivity. In the latex aggregation reaction, the aggregate exhibits the anisotropy and in particular, the scattered light emitted from a low concentration reaction liquid more remarkably exhibits the polarization dependency on the anisotropy. It is thus effective to measure the polarization state change between the incident state and the detection state, and the aggregation reaction can be measured with a higher sensitivity by measuring this polarization dependence.

The effects according to this embodiment will be described using a simulation result. An illustrative simulation will be shown. Assume that the reagent latex has spherical particles each having a diameter of 100 to 500 nm, and the reagent has a concentration of 0.1 to 0.5 mm$^{-1}$ (0.22 to 1.1 abs in terms of absorbance) with a scattering coefficient $\mu_s$. Assume that the aggregate contains two latex particles. In order to simplify the calculation, assume a spheroid whose shape is substantially the same as that of the aggregate, and a spherical particle having an equal sectional area is modeled as the aggregate. Assume that the antigen is sufficiently small relative to the latex particle.

The scattering calculation model presumes the Mie scattering, and the light propagation by the multiple scattering in the reaction liquid (scattering medium) is based on the transport equation. As the aggregation reaction proceeds, the volume ratio between the single latex particle and the aggregate is changed. At this time, according to the volume ratio, the scattering coefficient of the reaction liquid and the scattering phase function are respectively calculated and used for the propagation calculation. When the polarization is considered, the phase function is calculated for each polarization component. M. Xu, "Electric field Monte Carlo simulation of polarized light propagation in turbid media", Optics Express, Vol. 12, No. 26, 6530-6539 (2004) that expands the transport equation discloses the treatment of the polarization.

Assume that the incident light is linear polarization light with a wavelength of 600 nm. The polarization component (depolarization component) perpendicular (orthogonal) to the polarization of the incident light is calculated for the scattered light that has transmitted through and emitted from the reaction liquid. For comparison purposes, the nonpolarized light with the same wavelength is introduced into the reaction liquid, and the straight light component among the light having transmitted through and emitted from the reaction liquid, and the scattered light component at a scattering angle θ are similarly calculated.

Figure 1A:
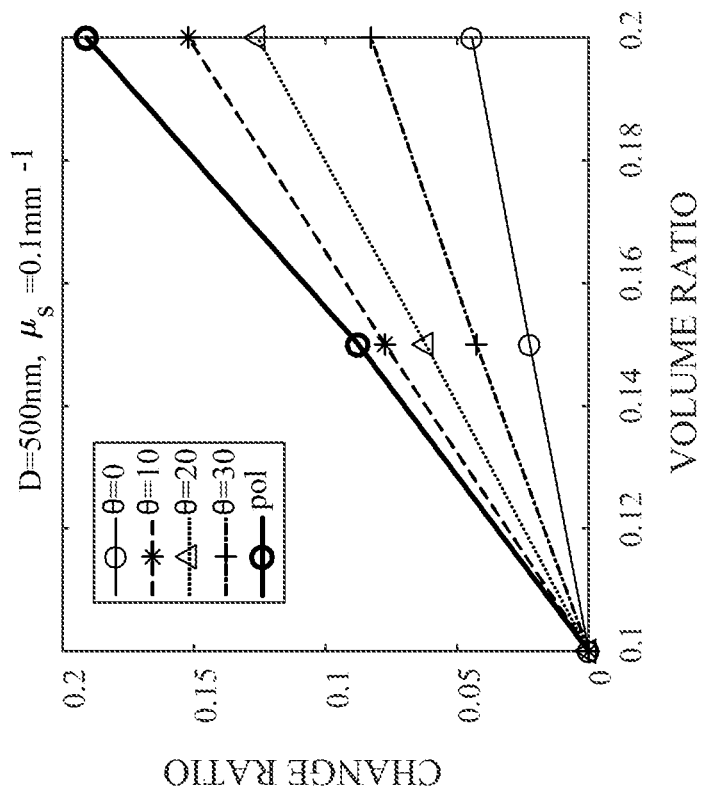

FIGS. 1A and 1B illustrate simulation results under the above condition. They assume that the aggregate already exists at a ratio of 10% in volume ratio when the object and the reagent are mixed (in the initial state). In the graphs of FIGS. 1A and 1B, the ordinate axis (change ratio) represents a signal change (change amount or change rate) due to the aggregation, calculated by finding (light intensity of volume ratio x−light intensity in initial state)/(light intensity in initial state) and by calculating the absolute value (x=0.1 to 0.2). The abscissa axis (volume ratio) represents the volume ratio of the aggregate and shows a range of 10% to 20%. In FIGS. 1A and 1B, "θ=0" means a signal change of the straight light (non-scattered light), and "θ=10", "θ=20", and "θ=30" indicates the signal changes of the scattering angles of 10°, 20°, and 30°. "pol" in FIGS. 1A and 1B indicates the signal change of the depolarization component. However, the depolarization component is the result made by summing up the scattered light in the angle range of θ=0° to 45°. FIG. 1A illustrates the calculation result on condition that the latex particle size is D=500 nm and the scattering coefficient is $\mu_s$=0.1 mm$^{-1}$, and FIG. 1B illustrates the calculation result on condition that D=100 nm and $\mu_s$=0.3 mm$^{-1}$.

In FIG. 1A, the signal change relative to the aggregate change when the scattered light (light emitted at the angle θ) is measured is larger than that when the straight light is measured, of the sensitivity is higher. The smaller the scattering angle is, the higher the sensitivity is. The depolarization component is even more sensitive than the scattered light. Depending on the latex particle size, a similar result can be obtained if the scattering coefficient is relatively small. On the other hand, in FIG. 1B, the straight light has the highest sensitivity, followed by the depolarization component and the scattered light (θ=10 to 30) in this order. Under this condition, the scattered light is less sensitive to the aggregation change.

As illustrated in FIGS. 1A and 1B, it is effective to measure the depolarization component when the reaction liquid has a low concentration (the scattering coefficient is small). On the other hand, when the reaction liquid has a high concentration, it is more effective to measure the straight light. The reversal phenomenon of the sensitivity between the depolarization component and the straight light component in the aggregation reaction depends on the concentration of the reaction liquid and on the latex particle size. When the particle size is large, the depolarization component is more sensitive than the straight light even at a relatively high concentration. Conversely, when the particle size is small, the straight light measurement tends to be more sensitive even at a low concentration.

The above tendency can be similarly confirmed by comparing the scattered light at an angle θ and the straight light with each other. In other words, the scattered light at the low concentration and the straight light at the high concentration are highly sensitive, and its concentration dependency also depends on the particle diameter. However, from the simulation result, the condition that the sensitivity is higher than the straight light can be confirmed in a wide range for the depolarization component (up to a higher concentration, to a wider range of particle diameter) rather than the scattered light at the angle θ.

Thus, the aggregation reaction can be quantified with a higher sensitivity in the reaction liquid having a relatively low concentration than the conventional scattered light measurement by measuring the depolarization component. For the high concentration reaction liquid, the measuring method is switched so as to measure the straight light instead of the depolarization component, whereby this method can handle the reaction liquid from the low concentration to the high concentration. It is also a characteristic of the present invention to switch and measure the polarized light measurement and the straight light measurement according to the concentration of the reaction liquid. In the measurement of the depolarization component, limiting the angular range of the scattered light to be detected provides a higher sensitivity to the aggregation reaction.

Figure 2:
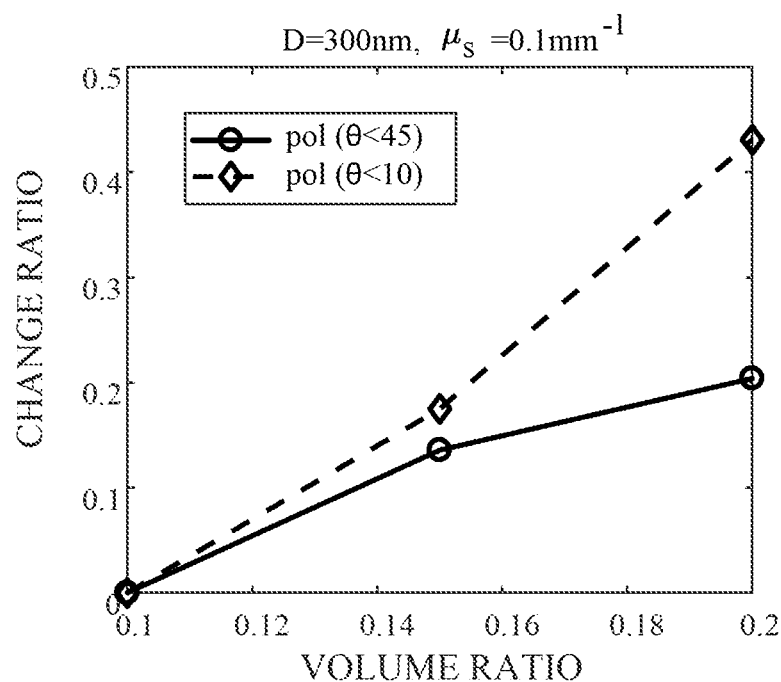
FIG. 2 illustrates another simulation result of the effect according to this embodiment.

FIG. 2 illustrates a comparison simulation result with a limited measurement angle for the signal change in the depolarization component as described above. In FIG. 2, "θ<45" and "θ<10" indicate an angle of 45° or less and an angle of 10° or less, respectively. The particle diameter is D=300 nm, and the scattering coefficient is $\mu_s$=0.1 mm$^{-1}$. Similar to the scattered light measurement at the angle θ, the depolarization component also has a high sensitivity by limiting the measurement range to the vicinity of the optical axis.

In general, the larger the scattering angle is, the larger the proportion of multiple scattered light is. Thus, the depolarization component becomes larger as the number of scattering times increases (the depolarization proceeds due to the multiple scattering). Thus, as the angle range is expanded, the depolarization component due to the scattering other than the aggregate also increase. In particular, when the volume ratio of the aggregate is small and the angle range is expanded, it is considered that the depolarized component become relatively large and the sensitivity to the aggregation reaction decreases as a result of multiple scattering of the single latex particles. Thus, the sensitivity can be further improved particularly at the low concentration and the small volume ratio of the aggregate, by measuring the depolarization component with the limited scattering angle.

However, the limited angle range reduces the light intensity detected by the detector and the SNR. Therefore, the angle may be limited in consideration of the balance between the sensitivity and the SNR. The simulation result shows that the sensitivity is further improved if the angle range is set to 10° or less. Alternatively, the sensitivity is also improved by limiting the angle to 10° or higher and 20° or lower.

Another measurement using the depolarization component can utilize the time variation of the signal intensity of the depolarization component. The dynamic light scattering is known as a method for analyzing temporal fluctuation of scattered light (temporal fluctuation). In the reaction liquid, the latex particles and their aggregates move in random directions by the Brownian motion. Small particles move relatively fast, and large particles move relatively slowly. Thus, when the temporal variation of the scattered light intensity emitted from the reaction liquid is evaluated using, for example, an autocorrelation function, the former is observed as a short correlation time (fast relaxation rate) and the latter as a long correlation time (slow relaxation rate). In general, this autocorrelation function can be expressed by an exponential function. The relaxation rate Γ corresponds to the attenuation coefficient of the exponential function, and is expressed as the following expression (1).

$$\Gamma = q^2 D \quad (1)$$

In the expression (1), q and D are expressed by the following expressions (2) and (3), respectively.

$$q = (4\pi n/\lambda)\sin(\theta/2) \quad (2)$$

$$D = k_B T / 3\pi\eta d \quad (3)$$

In the expressions (2) and (3), λ is a wavelength of light, n is a refractive index of the solution, θ is a scattering angle, $k_B$ is the Boltzmann constant, T is an absolute temperature, η is a solution viscosity, and d is a particle diameter (hydrodynamic size). Now assume that the wavelength λ of light, the refractive index n, the absolute temperature T of the solution, and the viscosity η of the solution are constant during the measurement. Then, the relaxation rate depends on the particle size d and the scattering angle θ. Further, when the scattering angle θ to be measured is fixed, the relaxation rate depends on the particle size d. Therefore, the aggregation reaction (aggregation degree) of the reaction liquid can be evaluated by measuring the relaxation rate Γ.

This embodiment selects the polarization of scattered light emitted from the reaction liquid, and analyzes the aggregation degree of the reaction liquid using the relaxation rate Γ of the autocorrelation function as the evaluation value for the time variation of the signal intensity of a specific polarization component. Alternatively, the diffusion coefficient D represented by the expression (3) or the particle size d may be used as the evaluation value. The shape of the autocorrelation function may be fitted with an arbitrary function, and a feature amount such as a fitting coefficient may be quantified to analyze the aggregation degree. The analysis of the time variation is not limited to the autocorrelation function, and may be an index that can evaluate the temporal change of the signal.

The measurement of this time variation is particularly effective to the reaction liquid having the relatively low concentration, and the aggregation reaction can be quantified with a higher sensitivity by analyzing the time variation of the depolarization component. On the other hand, when the reaction liquid has a high concentration, the signal intensity (transmittance) of the straight light (non-scattered light) may be measured. In this case, the signal intensity of the straight light can be measured which is non-polarized light or is not a depolarization component but a polarization component (polarization reserving component) parallel to the incident light. Thus, it is one of the characteristics of the present invention that not only the magnitude but also the time variation are considered for the signal intensity of the polarization component. Based on the above result, each embodiment of the present invention will be described below.

First Embodiment (Highly Sensitive Measurement Method in Low Concentration Area)

Figure 3:
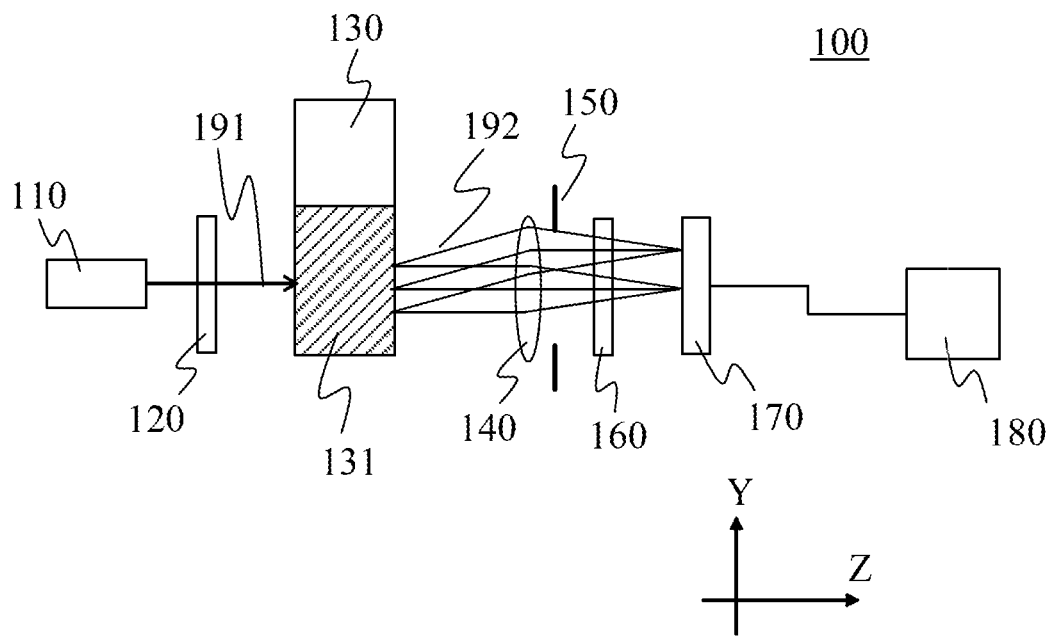
FIG. 3 is a block diagram of an automatic analysis apparatus according to the first embodiment.

Referring now to FIG. 3, a description will be given of an automatic analysis apparatus according to a first embodiment of the present invention. FIG. 3 is a block diagram of an automatic analysis apparatus 100 according to this embodiment. A light source 110 emits light with a wavelength in the visible band to the near-infrared band of 400 to 1100 nm, and uses an LED, for example. The wavelength of the light source 110 can be appropriately selected in accordance with the condition of the measuring object and the reagent. If necessary, light in the ultraviolet band with a wavelength of 400 nm or less or light in the infrared band with a wavelength of 1100 nm or higher may be used. The light source 110 may use a halogen lamp or a laser instead of the LED. This embodiment may use monochromatic light having a narrow wavelength width to some extent, but white light may be used if necessary.

The light source 110 emits parallel light, which passes through a polarization filter 120, and enters a reaction vessel (container) 130 as irradiation light 191 as linear polarization light. As one example, the irradiation light 191 is vertically incident on the reaction vessel 130. The reaction vessel 130 contains a reaction liquid 131 in which the measuring object and the reagent containing latex particles are mixed. The reaction liquid 131 has the aggregate of the latex particles at a certain ratio depending on the condition of the reaction liquid 131, such as the concentration of the measuring object, the particle size or concentration of the latex particles, or the reaction time after the measuring object and the reagent are mixed. Moreover, before the irradiation light 191 enters the reaction vessel 130, the reaction liquid 131 is agitated by an agitator (not shown), and single latex particles and aggregates are dispersed substantially uniformly in the reaction liquid.

Emitted light (including the straight light and scattered light) 192 that has propagated in the reaction liquid 131 and emitted from the reaction vessel 130 is focused by a lens 140, and is received by a detector 170 via an aperture 150 and a polarization filter (polarization selector) 160. The polarization filter 160 can arbitrarily control the polarization plane based on the condition of the reaction liquid 131. The detector 170 is a sensor sensitive to the wavelength band of the irradiation light 191. The detector 170 can use a single sensor such as a photodiode or an avalanche photodiode (APD) or an array sensor such as a CCD sensor or a CMOS sensor, but the present invention is not limited to this example. Herein, the intensity of the light emitted from the light source 110 can be appropriately adjusted according to the concentration of the measuring object or the reagent. For example, when the light intensity received by the detector 170 is small, the output of the light source 110 may be increased, and the reaction vessel 130 may be irradiated with irradiation light 191 of a higher intensity.

A signal output from the detector 170 is transferred to a processor 180 including a memory and its data is processed. The measurement is performed over time (reaction time) from the time (initial state) when the measuring object and the reagent are mixed, and the processor 180 acquires data according to the elapse. The processor 180 stores the acquired and transferred data in the memory as needed, and analyzes and processes while appropriately reading the data, thereby quantifying the concentration of the measuring object in the reaction liquid 131. The quantified result may be output to a display unit such as a monitor.

The automatic analysis apparatus 100 controls the polarization plane of the polarization filter (polarization selector) 160 based on the condition of the reaction liquid 131. When the reaction liquid 131 has the low concentration, as described above, the aggregation reaction can be measured with a high sensitivity by detecting the depolarization component. Thus, in this case, the polarization filter 160 sets the polarization plane of the polarization filter 160 so that the polarization plane of the polarization filter 120 and the polarization plane of the polarization filter 160 are perpendicular to each other. In other words, the detector 170 receives the depolarization component (perpendicular component) of the emitted light 192. The aperture 150 may be open or narrowed to measure the depolarization component of the component close to the straight light.

On the other hand, when the reaction liquid 131 has a high concentration, it is more effective to measure the straight light (non-scattered light) component. Therefore, the polarization filter 160 sets the polarization plane of the polarization filter so that the polarization plane of the polarization filter 120 and the polarization plane of the polarization filter 160 are parallel to each other. The detector 170 then measures the polarization reserving component (parallel component). At this time, the aperture 150 may be set so that the detector 170 can substantially receive the straight light component almost dominantly.

Thus, the control over the polarization selector (polarization filter 160) according to the condition of the reaction liquid 131 is one of the characteristics of this embodiment. However, the condition of the reaction liquid 131 is not limited to the concentration of the measuring object, the particle size and concentration of latex particles, or the reaction time after the measuring object and the reagent are mixed, and may use other conditions.

Depending on the concentration of the reaction liquid 131, it is calibrated in advance using a standard solution as to the timing to switch the measurement of the depolarization component and the measurement of the straight light. The standard solution is a solution in which the measuring object whose concentration and size are known, and the reagent are mixed with each other. The measurement is performed in advance using the standard solution, and how the depolarization component for the concentration of the solution and the light intensity of the straight light change are acquired as calibration data.

Figure 4:
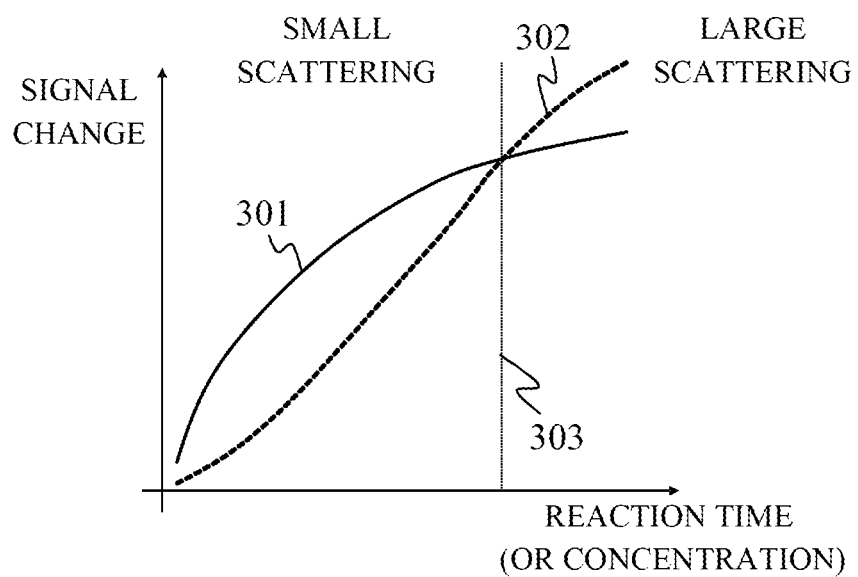
FIG. 4 illustrates a relationship between a concentration of a reaction liquid and a signal change according to the first embodiment.

FIG. 4 is a schematic view of the calibration data, showing the relationship between the concentration of the reaction liquid 131 and the signal change. In FIG. 4, the abscissa axis represents the reaction time, and the ordinate axis represents the signal change (change amount) in the aggregation reaction. In FIG. 4, reference numeral 301 denotes calibration data of the depolarization component, and reference numeral 302 denotes calibration data of the straight light component. In the calibration data 301, the signal changes with a high sensitivity to an aggregation change in a region where scattering is relatively small. On the other hand, in the calibration data 302, the signal changes with a high sensitivity in a region where the scattering is relatively large. In the aggregation state 303 at a certain reaction time, the sensitivities (signal changes) of the calibration data 301 and 302 are reversed. Based on the calibration data 301 and 302, the signal change determined by the state of the reaction liquid 131 is monitored, and the polarization direction of the polarization filter 160 is determined so as to measure the signal with a larger signal change. The aperture 150 may be controlled as needed.

Alternatively, the polarization filter 160 may be sequentially switched to measure two data of the depolarization component and the straight light component at substantially the same reaction time, and to select a signal in the analysis. In other words, as illustrated in FIG. 4, the processor 180 analyzes the sensitivity (signal change) to the aggregation change for the two measurement data, and selects the signal with a higher sensitivity to analyze the measuring object. Herein, the abscissa axis in FIG. 4 may be the concentration of the reagent or reaction liquid 131. In other words, the depolarization component is measured on the lower concentration side (the scattering is relatively small) than the aggregation state (concentration) 303 of a certain reaction liquid 131, and the straight light component is measured on the higher concentration side. Hence, the polarization filter (polarization selector) 160 selects the polarization direction to be measured or analyzed based on the signal change determined according to the condition or state of the reaction liquid 131.

In this embodiment, the condition of the reaction liquid 131 include at least the following two conditions. One is a condition determined by the initial condition of the measurement, such as the size and concentration of the measuring object, or the particle diameter and concentration of the reagent (latex particle), the type of the reagent, and the information of the measurement item. The other one is a state of the aggregation in the reaction liquid during the measurement depending on the elapsed time after the reaction starts, and is a condition determined based on the measurement data of the reaction liquid.

This embodiment particularly addresses a change (change ratio) between a signal at the start of measurement and a signal after an elapse of a certain reaction time as represented by the above signal change (change ratio) according to the condition of the reaction liquid 131. More specifically, it is one of the characteristics of the present invention to select the polarization direction, to measure and analyze the signal so that the signal change becomes large (sensitivity becomes high) according to the condition of the reaction liquid 131.

(First Variation: Measurement of Depolarization Component with Limited Angle)

Next follows a description of a first variation of this embodiment. As described with reference to FIG. 2, the measurement sensitivity of the depolarization component can improve by limiting the angle of the scattered light to be measured to a low angle near the optical axis. Therefore, in the measurement of the depolarization component, the aperture 150 may be narrowed and the measurement may be made at a limited angle. However, the limited angle reduces the light amount received by the detector 170 and degrades the SNR. It is thus necessary to control the aperture 150 while the balance is considered between sensitivity and SNR. Herein, in order to improve the light amount received by the detector 170, the output of the light source 110 may be increased. The control over the aperture 150 may include a calibration measurement using a standard solution in advance to find an aperture size appropriate for the reaction condition.

Figures 5A, 5B, 5C:
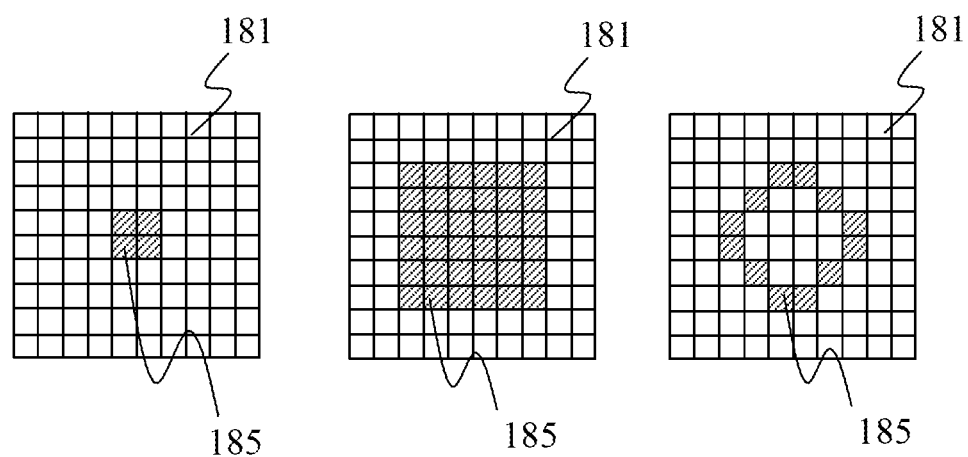
FIGS. 5A to 5C explain a measurement method by an array sensor pixel selection according to the first embodiment.

If an array sensor is used for the detector 170, the angle may be limited by the pixel selection on the sensor as illustrated in FIGS. 5A to 5C, instead of controlling the aperture 150. FIGS. 5A to 5C are explanatory diagrams of a measurement method by a pixel selection of the detector (array sensor) 170. Each of the reaction vessel 130 and the detector (array sensor) 170 is placed at the focal position of the lens 140, and the angular distribution of the emitted light 192 is measured on the detector 170. Thus, the measurement angle is limited based on the angle corresponding to the pixel position on the array sensor.

In FIGS. 5A to 5C, reference numeral 181 denotes a pixel on the sensor, and reference numeral 185 denotes a measurement pixel (beveled area). For example, in FIG. 5A, the measurement pixel 185 is limited to the vicinity of the center to measure an angular component near the optical axis for the depolarization component or the polarization reserving component. On the other hand, the angular range of the emitted light 192 can be made wider to be measured by widening the area of the measurement pixel 185 as illustrated in FIG. 5B. Alternatively, as illustrated in FIG. 5C, the measurement pixel 185 may be set concentrically with respect to the optical axis (pixel center), and the emitted light in a specific angle range (for example, $10°<\theta<20°$) may be measured.

Thus, the measurement pixel 185 can be arbitrarily set for the pixel 181 on the sensor. In practice, data of all pixels on the sensor may be acquired, and processing may be performed using only data of the measurement pixel 185 in the analysis in the processor 180. The data measured in the concentric circles (approximately the same scattering angle) as illustrated in FIG. 5C can be compared to verify the reliability of the data. For example, when the values of measurement data at a plurality of pixel positions corresponding to substantially the same scattering angle are significantly different, it may be determined that this is because of the noise source other than the aggregate (such as air bubbles), and data processing may be performed after the signal at that pixel position is removed. For example, an average value or a median value of the measurement data described above may be set to a reference value to be removed as the noise, where a standard deviation of the measurement data may be determined as the reference value, and the data above or below a threshold that is a times (constant) as large as the standard deviation may be removed.

(Second Variation: Scattered Light Distribution Measurement Using Array Sensor)

Next follows a description of a second variation of this embodiment. The light emitted from the reaction liquid 131 includes the transmitted light of the non-scattering component and the scattered light scattered by the single latex particle and the aggregate thereof. In particular, when the reaction liquid 131 has a low concentration, the former is more intense than the latter. Hence, if the light emitted from the reaction liquid 131 is received by the array sensor as it is, the intensity of the transmitted light is too high to measure the scattered light intensity because the dynamic range is insufficient with a normal array sensor. On the other hand, the non-scattered light can be cut by providing the polarization filter (polarization selector) so as to receive the emitted light of the depolarization component as in this variation. As a result, since only the scattered light can be received by the array sensor, the above problem of the lack of the dynamic range is eliminated. Thus, the spatial distribution of the scattered light can be analyzed from the measurement results received by the array sensor.

Thus, in addition to the light intensity of the depolarized scattered light, the reaction liquid 131 may be analyzed including the spatial distribution of the scattered light. In particular, when the reaction liquid 131 has a low concentration, the irradiation light 191 is less likely to be scattered in the process of propagating in the reaction liquid 131, and the influence of multiple scattering is small. Thus, the scattered light distribution by the single scattering remarkably appears. In other words, the array sensor can detect the characteristic intensity distribution of the scattered light caused by the aggregate anisotropy. On the other hand, as the concentration of the reaction liquid becomes higher, the influence of the multiple scattering is increased, and the intensity distribution of the scattered light becomes a distribution obtained by averaging the intensity distribution caused by the individual scattering. Thus, it becomes difficult to measure the characteristic scattered light distribution due to the anisotropy.

A combination of the polarization filter (polarization selector) 160 and the detector (array sensor) 170 can measure the spatial light intensity distribution of the scattered light corresponding to the aggregation change. The polarization filter (polarization selector) 160 may be set to be perpendicular to the incident light polarization as described above, and the depolarization component may be received by the detector (array sensor) 170. However, the polarization filter may be set to be parallel to the incident light polarization, or may be set in an arbitrary direction to measure the scattered light distribution with the array sensor. The measurement result may be analyzed by the processor 180 and used for the analysis of the measuring object.

The array sensor is not limited to the above configuration, and may use, for example, an array sensor having an image intensifier. Alternatively, a sensor that can detect weak light with a high sensitivity may be used, such as an EMCCD (Electron-Multiplying CCD), an sCMOS (Scientific CMOS), or a SPAD (Single-Photon Avalanche Diode) array.
(Third Variation)

Figure 6A:
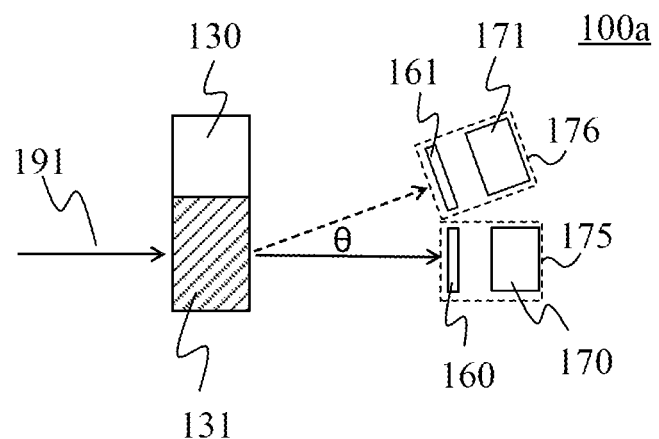
FIGS. 6A and 6B are block diagrams of another automatic analysis apparatus according to the first embodiment.
Figure 6B:
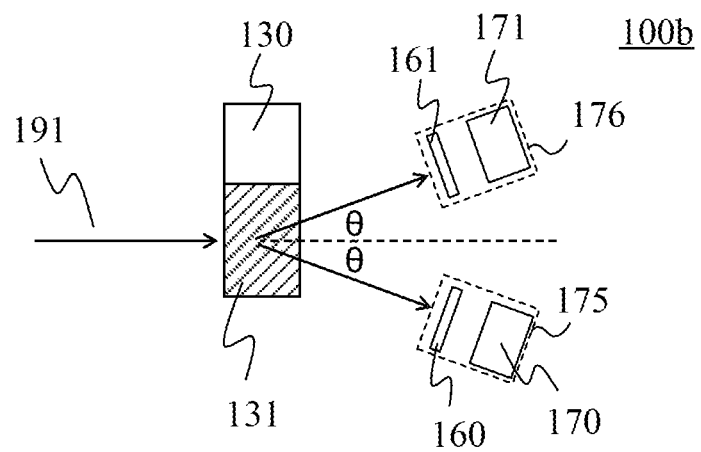

Next follows a third variation according to this embodiment. FIGS. 6A and 6B are block diagrams of automatic analysis apparatuses 100a and 100b, respectively, according to this variation. The automatic analysis apparatus may have a plurality of measurement units including the polarization filter 160 and the detector 170 for the reaction vessel 130. As illustrated in FIGS. 6A and 6B, each of the automatic analysis apparatuses 100a and 100b according to this variation includes a measurement unit 175 including the polarization filter 160 and the detector 170, and a measurement unit 176 including a polarization filter 161 and a detector 171.

In FIG. 6A, the measurement unit 175 including the polarization filter 160 and the detector 170 is placed on the optical axis ($\theta$=0) of the irradiation light (incident light) 191. On the other hand, the measurement unit 176 including the polarization filter 161 and the detector 171 is placed at a certain angle $\theta$ relative to the optical axis from the transmission plane of the reaction vessel 130. The plurality of measurement units 175 and 176 can simultaneously measure different measurement conditions.

For example, the polarization filters 160 and 161 are set to be parallel and perpendicular to the polarization plane of the polarization filter 120, respectively. The detector 170 measures the polarization reserving component, which is the directly transmitted light component. The detector 171 measures the depolarization component in the scattered light scattered at the angle $\theta$. The angular range is appropriately set by controlling the respective apertures. Thus, according to the condition of the reaction liquid 131, the processor 180 may select the measurement result with a higher sensitivity to the aggregation reaction and quantify the measuring object while simultaneously measuring the depolarization component and the straight light (non-scattered light) by the two detectors. Alternatively, the depolarization components of the scattered light may be measured simultaneously by a plurality of measurement units (i.e., the polarization planes of the polarization filters 160 and 161 are set to be perpendicular to the polarization plane of the polarization filter 120). The configuration illustrated in FIG. 6A may use the lens 140 illustrated in FIG. 3, or may directly measure the emitted light by the polarization filter and the detector.

Figure 7:
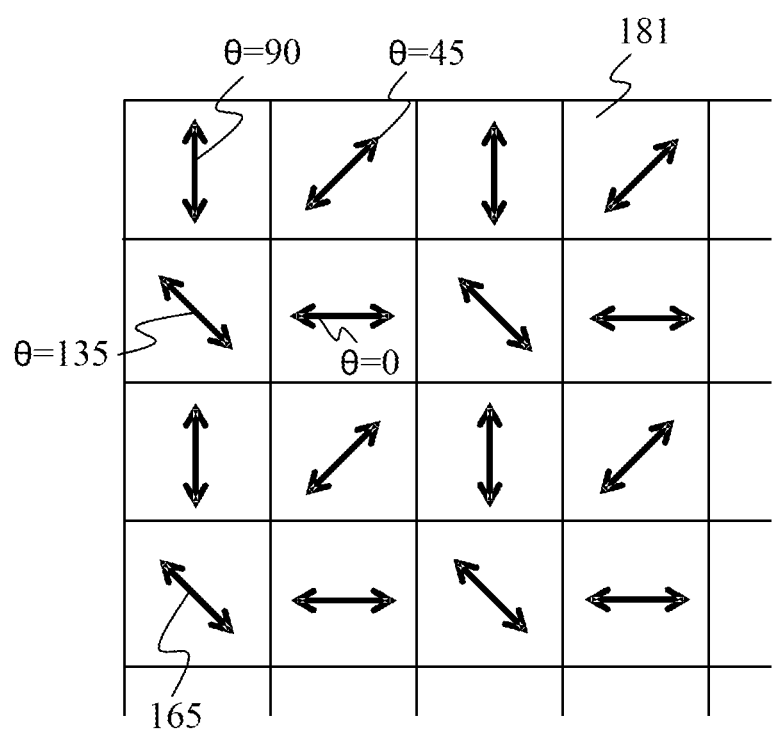
FIG. 7 is a schematic view of the array sensor according to the first embodiment.

Instead of using the polarization filter 160, the polarization selector may use a sensor configured to receive light in a specific polarization direction 165 in pixel unit by disposing a fine polarizer on the pixel structure of the detector (array sensor) 170, as illustrated in FIG. 7. FIG. 7 is a schematic view of the detector (array sensor) 170.

It is also possible to simultaneously measure polarization components parallel ($\theta$=0°) and perpendicular ($\theta$=90°) to the linear polarization of the incident light, and to analyze with a limited angle corresponding to the pixel position as described above. When the reaction liquid 131 has a low concentration, the light intensity is largely different between the straight light component (polarization reserving component) and the depolarization component, and thus the exposure time may be changed and the measurement may be performed multiple times. For example, the measurement is performed twice by changing the exposure time, the straight light component ($\theta$=0°) is extracted from the data measured with the shorter exposure time, and the depolarization component ($\theta$=90°) is extracted from data measured with the longer exposure time. Here, by using the measurement results of the polarization directions of 0°, 45°, 90°, and 135° measured by the array sensor in FIG. 7, the linear polarization degree DoLP may be calculated based on the following expressions (4) to (7), and the aggregation reaction may be analyzed.

$$S_0 = I(0) + I(90) \tag{4}$$

$$S_1 = I(0) - I(90) \tag{5}$$

$$S_2 = I(45) - I(135) \tag{6}$$

$$DoLP = \frac{\sqrt{S_0^2 + S_1^2 + S_2^2}}{S_0} \tag{7}$$

Alternatively, even if the configuration cannot select the polarization in pixel-wise as described above, it can be possible to have the same function. For example, the configuration may be made in such a way that a region is divided for a normal array sensor, and a different polarization filter illustrated in FIG. 7 is disposed in each region (region including a plurality of pixels). As described above, since the light intensity significantly differs between the straight light component (polarization reserving component) and the depolarization component, for example, the intensity may be adjusted using an ND filter in the region for detecting the straight light component. The light intensities of the straight light component and the depolarized component may be adjusted within the dynamic range of the detector (array sensor) 170, and these components may be measured simultaneously.

In addition, particularly when the reaction liquid 131 has a low concentration and the latex particle size is small, the scattered light is weak and a weak light detection such as lock-in detection is effective. In other words, a signal generator is used to electrically generate a reference signal to be modulated at a predetermined frequency, and the irradiation light 191, which is light made by temporally modulating the intensity of the light emitted from the light source 110, is introduced into the reaction vessel 130 by using this reference signal. The lock-in detection may be performed for the emitted light 192 by using the reference signal. The intensity may be modulated by using a modulation device such as an electro-optic modulator, or by controlling a current to be injected by a driver in a light source such as a semiconductor laser. The gain of the detector 170 may be modulated for the heterodyne detection.

This embodiment has described the measurement unit 175 including the polarization filter 160 and the detector 170 in the transmitted light measurement configuration that measures the light that has transmitted through and emitted from the reaction vessel 130, but the present invention is not limited to this configuration. For example, the present invention is applicable to scattered light emitted from the side surface, top surface, or bottom surface of the reaction vessel 130 or backscattered light, which is scattered to the light source 110 side. The measurement of the depolarization component need not always use the linear polarization. For example, in using circularly polarized light as incident polarized light and measuring the depolarization component, the measurement may be performed for polarized light orthogonal to the circularly polarized light of the incident light (circularly polarized light in the reverse direction).

This embodiment may measure and process a non-polarized light signal (no polarization filter 160), instead of the polarization reserving component.

(Fourth Variation: Analysis of Time Variation)

Next follows a description of a fourth variation according to this embodiment. In FIG. 3, the detector 170 is a sensor that is sensitive to the wavelength band of the irradiation light 191 and has a relatively high response speed. For example, the detector 170 may use a photodiode, an APD, or the like, or a quickly responsive array sensor (two-dimensional array sensor). Herein, the time resolution of the measurement may be 1 μsec or less, such as about 100 nsec. The light intensity of the time-varying depolarization component is measured, and the measurement data is sequentially transferred to the memory.

The processor 180 reads time variation data of the light intensity and calculates an autocorrelation function as a function of the time interval τ. This may be repeatedly measured within the measurement time and averaged, and the autocorrelation function may be calculated. A characteristic quantity, such as the relaxation rate, is calculated from the autocorrelation function, and set to an evaluation value of the aggregation degree of the reaction liquid during the measurement (the elapsed time of the reaction). Thus, the evaluation value is measured with the elapsed time of the reaction after the measuring object and the reagent are mixed, and the aggregation reaction is quantified.

On the other hand, when the reaction liquid 131 has a particularly high concentration, it may be more effective to measure the signal intensity (temporal average value) or the transmittance of the straight light (non-scattered light) component. At this time, the polarization filter 160 sets its polarization plane to be parallel to the polarization plane of the polarization filter 120. The detector 170 then measures the polarization reserving component (parallel component). The aperture 150 may be narrowed so as to enable the detector 170 to receive a substantially straight light component in a substantially dominant manner.

According to the expressions (1) and (2), the relaxation rate Γ becomes larger as the scattering angle θ becomes larger, even with the same particle size d. In other words, the particle size can be evaluated in a relatively short correlation time. Thus, the scattering angle θ may be appropriately set according to the latex particle size and the measurement time, and the detector 170 may be placed at a position having the same angle. Alternatively, a plurality of detectors 170 and 171 may be prepared in advance according to the scattering angle θ, the detector may be selected according to the above condition, and the autocorrelation function of the signal may be analyzed. When the array sensor is used as a detector, the signal may be analyzed by selecting a pixel corresponding to the scattering angle θ.

Herein, the aggregation degree of the reaction liquid may be evaluated based on two measured values of signal intensity (temporal average value) of depolarization light intensity and its temporal fluctuation (such as the relaxation time Γ). In using a plurality of detectors 170 and 171, the aggregation degree may be analyzed by arbitrarily combining signals having a high sensitivity to the aggregation reaction. In other words, the array sensor using a polarization filter (polarization selector) can detect the characteristic spatial intensity distribution of the scattered light caused by the anisotropy of the aggregate. In addition to this spatial distribution, the scattered light can be analyzed according to the aggregation change by combining the above temporal fluctuations.

For example, as illustrated in FIG. 6A or 6B, the polarization filter 160 and the detector 170 for measuring the spatial distribution of the depolarization component, and the polarization filter 161 and the detector 171 for measuring the time variation may be separately provided. As illustrated in FIGS. 6A and 6B, the axis of the detector 171 is positioned at an arbitrary angle θ relative to the detector 170. The detector 170 can measure the spatial distribution of the scattered light, the detector 171 can measure the temporal variation of the scattered light, and the processor 180 can analyze the results. Alternatively, the detector 170 may simultaneously measure the spatial distribution and the time variation without using the detector 171. For example, the temporal variation may be measured according to the spatial distribution of the scattered light. At this time, the temporal fluctuation of the signal may be analyzed in the characteristic scattering direction in which the signal intensity is high.

For example, as illustrated in FIG. 6B, both of the detectors 170 and 171 may be configured to measure the scattered light: One of them may measure the signal intensity of the polarization reserving component and the other of them may measure the signal intensity of the depolarization component. For example, in order to reduce the system error of the measurement system, the aggregation degree may be analyzed by a difference or a comparative evaluation, such as a relative ratio, between the relaxation time $\Gamma_1$ calculated from the signal of the polarization reserving component and the relaxation time $\Gamma_2$ calculated from the signal of the depolarization component. The detectors 170 and 171 may be set to the same scattering angle, or may be set to different scattering angles.

The polarization filters (polarization selector) 160 and 161 may be set to be perpendicular to the incident light polarization as described above, and the detector (array sensor) 170 may receive the depolarization component. However, the polarization filters 160 and 161 may be set so as to be parallel to the incident polarized light, or the array sensor may measure the scattered light distribution by setting them in any directions.

Second Embodiment (Simultaneous Monitoring and Measuring Method of Two Polarized Lights)

Figure 8:
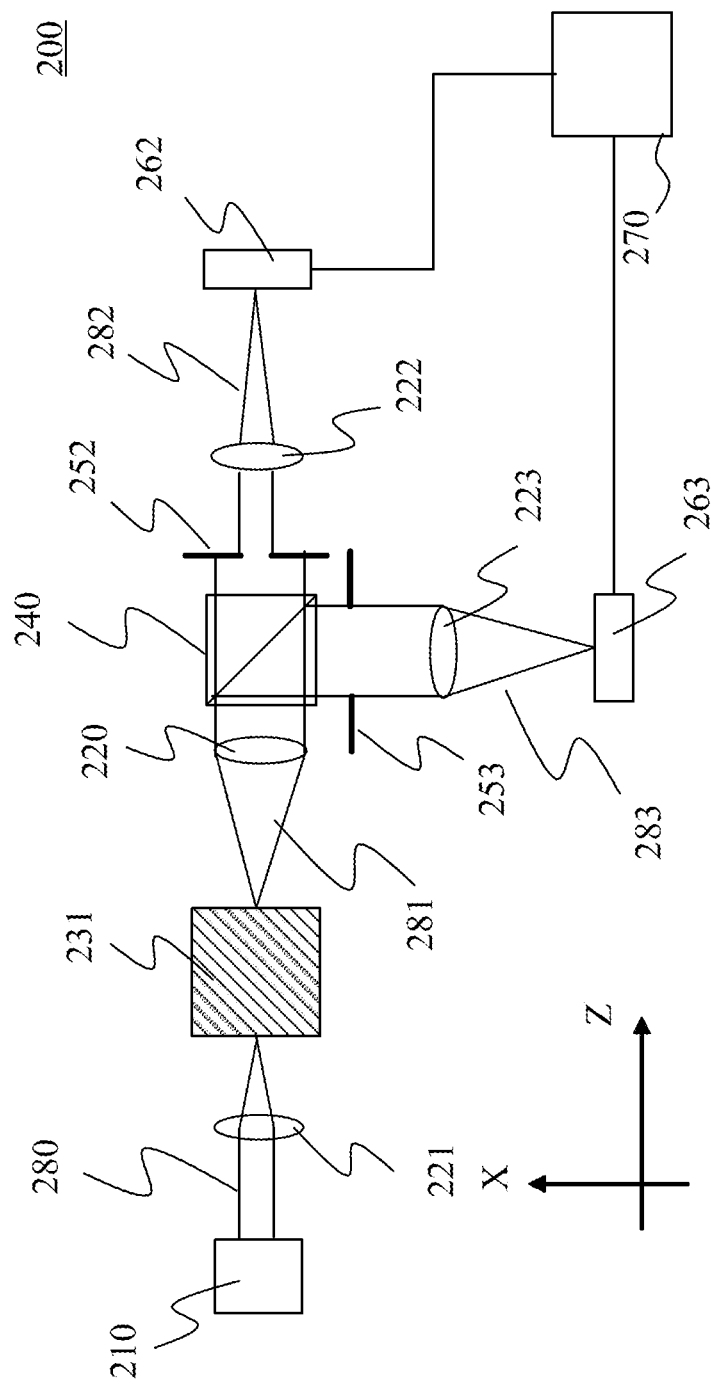
FIG. 8 is a block diagram of an automatic analysis apparatus according to a second embodiment.

Next follows a description of an automatic analysis apparatus according to a second embodiment of the present invention. FIG. 8 is a block diagram of an automatic analysis apparatus 200 according to this embodiment. A light source 210 is a laser that outputs visible light, and emitted light 280 from the light source 210 is parallel light and linear polarization light. The emitted light 280 is collected by a lens 221 and enters a reaction liquid 231. Herein, the emitted light 280 may be vertically or obliquely incident on the reaction liquid 231. In addition, the beam diameter may be expanded to irradiate the reaction liquid 231 so that substantially the entire reaction liquid 231 can be irradiated with parallel light instead of the focused irradiation. Instead of the light source 210, the light source 110 and the polarization filter 120 as illustrated in FIG. 3 may be used.

Transmitted light 281 that has transmitted through the reaction liquid 231 is split by a polarization beam splitter 240 into a polarization component 282 parallel to the incident light polarization of the incident light 280 and a polarization component 283 perpendicular to the incident light 280 via the lens 220. For each of them, similar to the first embodiment, the angular range measured by the apertures 252 and 253 are appropriately adjusted. Emitted light fluxes 282 and 283 pass through lenses 222 and 223 and are collected on detectors 262 and 263, respectively. The output signal of each of the detectors 262 and 263 is transferred to a processor 270. The processor 270 processes the output signal of each of the detectors 262 and 263 to quantify the concentration of the measuring object in the reaction liquid 231. Instead of the polarization beam splitter 240, a beam splitter and a polarization filter may be used to separate the polarization component parallel to the incident light and the polarization component perpendicular to the incident light.

The processor 270 acquires both of the emitted light flux 282 (polarization reserving component) in which the non-scattered light is dominant and the emitted light flux 283 (depolarization component) in which the scattered light is dominant in the transmitted light 281 as the reaction time elapses by the parallel (simultaneously) measurements at the same timing. The angle range is set, for example, by setting both of the emitted light fluxes 282 and 283 to a low angle substantially near the optical axis. Alternatively, while the signal levels from each of the detectors 262 and 263 are confirmed, the angle range may be expanded independently if necessary. While both signals are monitored, measurement data having a large signal change during the reaction time can be employed, and the measuring object in the reaction liquid 231 can be quantified based on the signal change. At this time, similar to the first embodiment, a relationship between the concentration of the measuring object and the signal change may be previously measured as calibration data, and the measurement data may be selected based on the calibration data.

Alternatively, the signal intensity and its time variation may be analyzed for the depolarization component 283, while the signal intensity may be analyzed for the polarization preserving component 282. The simultaneous measurement of two polarization directions can quantify the concentration of the measuring object for the reaction liquid with a variety of concentrations. Alternatively, the time variation may be analyzed for the polarization reserving component. This embodiment may apply the configuration using the array sensor described in the first embodiment.

Third Embodiment (Example Incorporated into Rotary Type Automatic Analysis Apparatus)

Figure 9:
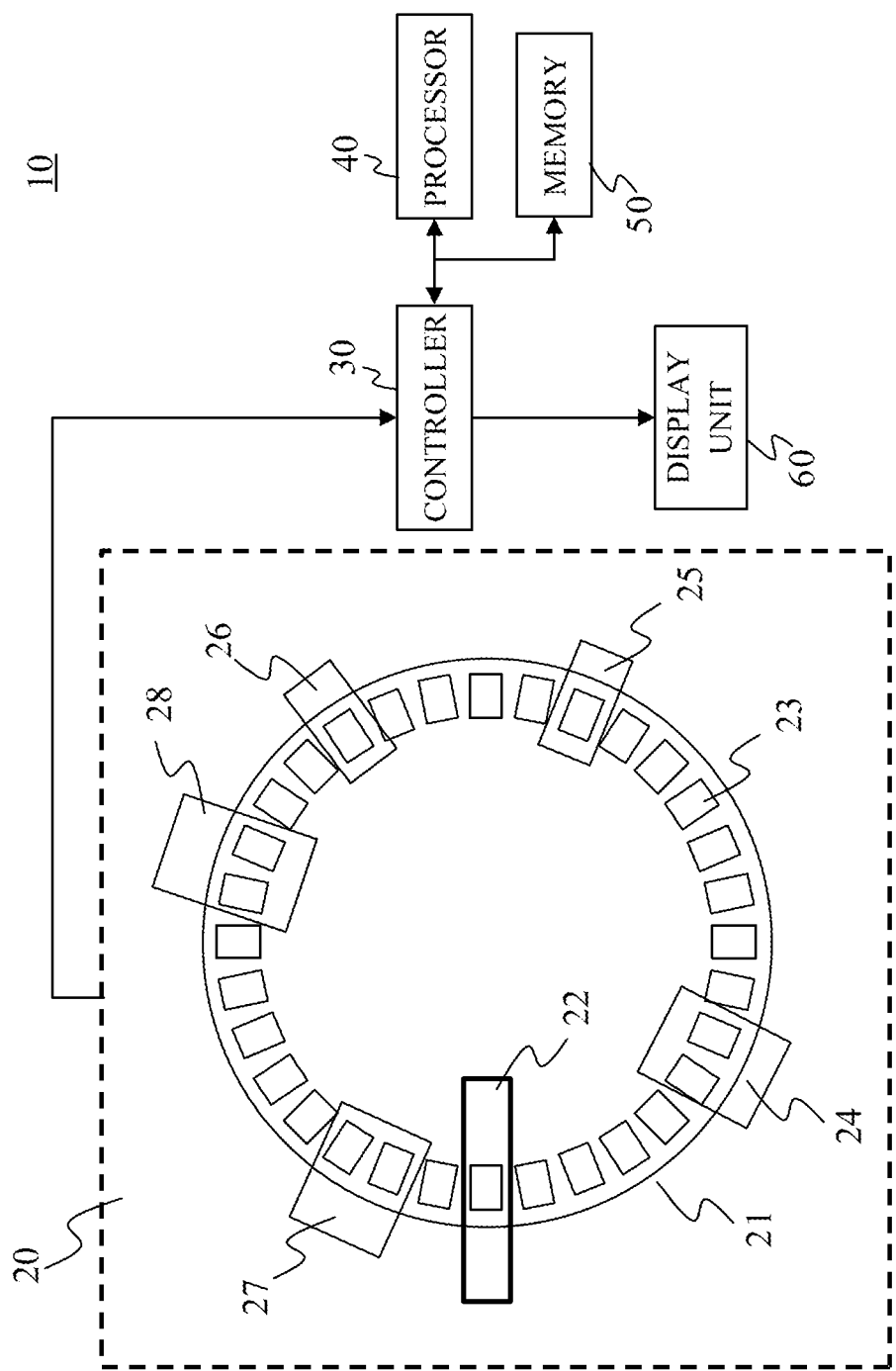
FIG. 9 is a block diagram of an automatic analysis apparatus according to a third embodiment.

Next follows a description of a third embodiment according to the present invention. FIG. 9 is a block diagram of an automatic analysis apparatus 10 according to this embodiment. The automatic analysis apparatus 10 has an analyzer 20 and a controller 30 that controls the analyzer 20, as disclosed in JP 2015-7649. The controller 30 controls a measurement flow in a measurement unit 22, receives a signal output from the measurement unit, controls a processor 40 and a memory 50, and executes data transfer, processing, and storage. The automatic analysis apparatus 10 further includes a display unit 60 that displays the result processed by the processor 40.

The analyzer 20 includes a rotatable disc 21 and a plurality of reaction vessels 23 arranged on the circumference of the disc 21. A measurement unit 22 performs the measurement described later for the rotatable reaction vessel 23 that has passed the light measurement position. The analyzer 20 is a sample dispenser 24 that dispenses a sample such as a standard sample (standard solution) or a measuring object into the reaction vessel 23, and a first reagent dispenser 25 that dispenses a first reagent that reacts with a component contained in the sample, and a second reagent dispenser 26 configured to dispense a second reagent paired with the first reagent. The analyzer 20 further includes an agitator 27 for agitating a mixed solution obtained by mixing a sample and a reagent, and a washer and dryer 28 for sucking the post-measurement mixed solution from the reaction vessel 23 to wash and dry the inside of the reaction vessel 23. Hence, the automatic analysis apparatus 10 can continuously carry out a series of flows from the sample and reagent dispensing, the agitation, the measurement, the suction, the washing and drying while rotating the disc 21. The reaction vessel 23 is housed in a constant temperature bath, and the temperature of the reaction liquid is kept constant.

Figure 10A:
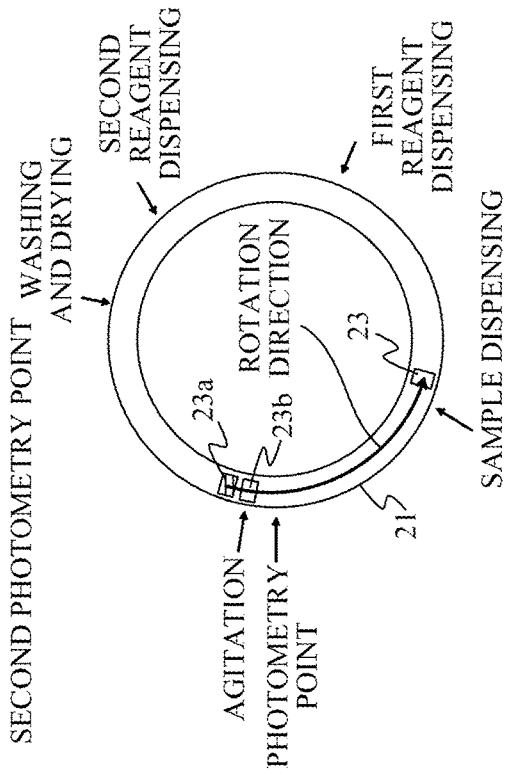
FIGS. 10A to 10C illustrate photometry points of a measurement unit and a rotation of a disc according to the third embodiment.
Figure 10B:
Figure 10C:
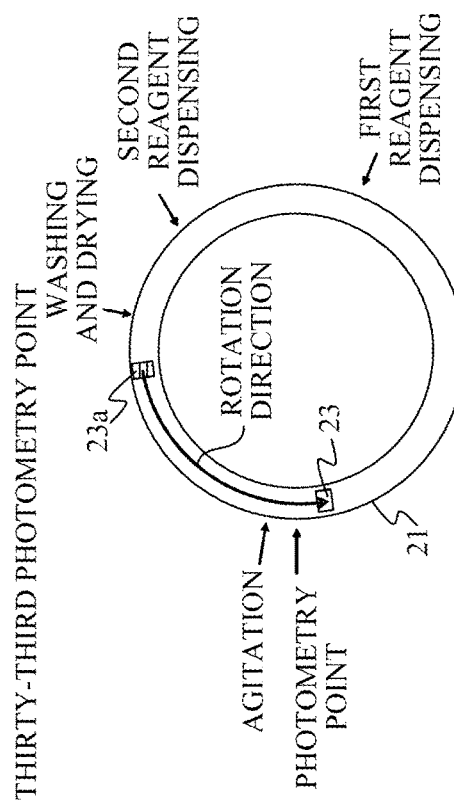

FIGS. 10A to 10C schematically illustrate the photometry (light measuring) point of the measurement unit 22, the reaction vessel 23, and the rotation of the disc 21. As illustrated in FIG. 10A, after the agitator 27 agitates the solution in a reaction vessel 23a (agitation position), the disc 21 is rotated by 90° from the agitation position and the measurement is made when the disc 21 passes the photometry point (position of the measuring unit 22). Now assume that a first photometry point is set to the reaction vessel 23a, when the disc 21 rotates and passes the photometry position for the first time, and the measurement is made. Thus, FIG. 10A illustrates a rotation start position of the reaction vessel 23a for measuring the first photometry point.

When the reaction vessel 23a makes one revolution on the disc and returns to the agitator again, as illustrated in FIG. 10B, it is shifted in the direction opposite to the rotation direction of the disc 21 by the pitch of the adjacent reaction vessel (reaction vessel 23b adjacent to the reaction vessel 23a comes to the agitation position). From this state, when the disc 21 is rotated again by 90° and passes through the photometry position, the measurement is similarly performed to obtain the measurement data at the second photometry point for the reaction vessel 23a. Hence, FIG. 10B illustrates the rotation start position of the second photometry point. As described above, the process is repeated which rotates the disc 21 every 90° and shifts the pitch for each one revolution, and the sample and the reagent are automatically dispensed, agitated, and measured. FIG. 10C illustrates the rotation start position of the reaction vessel 23a that measures the thirty-third photometry point.

Figure 11:
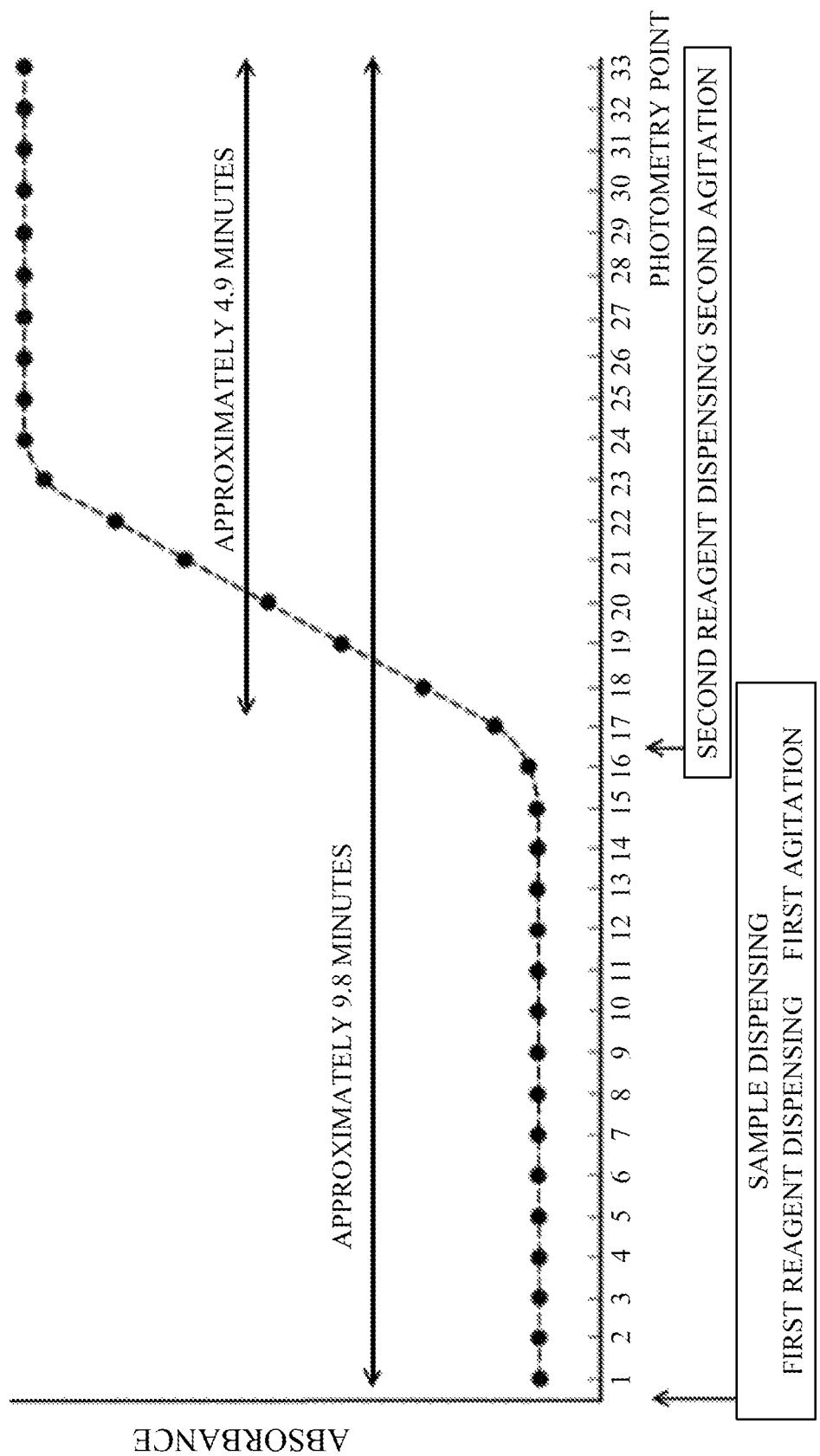
FIG. 11 illustrates exemplary measurement results at the photometry points with the latex aggregation reaction according to the third embodiment.

When the measurement data is acquired at the photometry timing described above, the measurement result of each photometry point and the latex aggregation reaction are exemplarily illustrated in FIG. 11. FIG. 11 illustrates an exemplary measurement result by a photometry point and latex aggregation reaction. In FIG. 11, the abscissa axis indicates the first to thirty-third photometry points, and the ordinate axis indicates the absorbance as one of the measurement data measured by the measurement unit 22. In this embodiment, the sample and the first reagent are dispensed and agitated in the reaction vessel just before the first photometry point to start measurement, and the second reagent is dispensed and agitated just before the seventeenth photometry point. The measurement ends at the thirty-third photometry point. Since the latex aggregation reaction starts after the second reagent is dispensed, the aggregation reaction is quantified based on the measurement results of the seventeenth to thirty-third photometry points.

Figure 12:
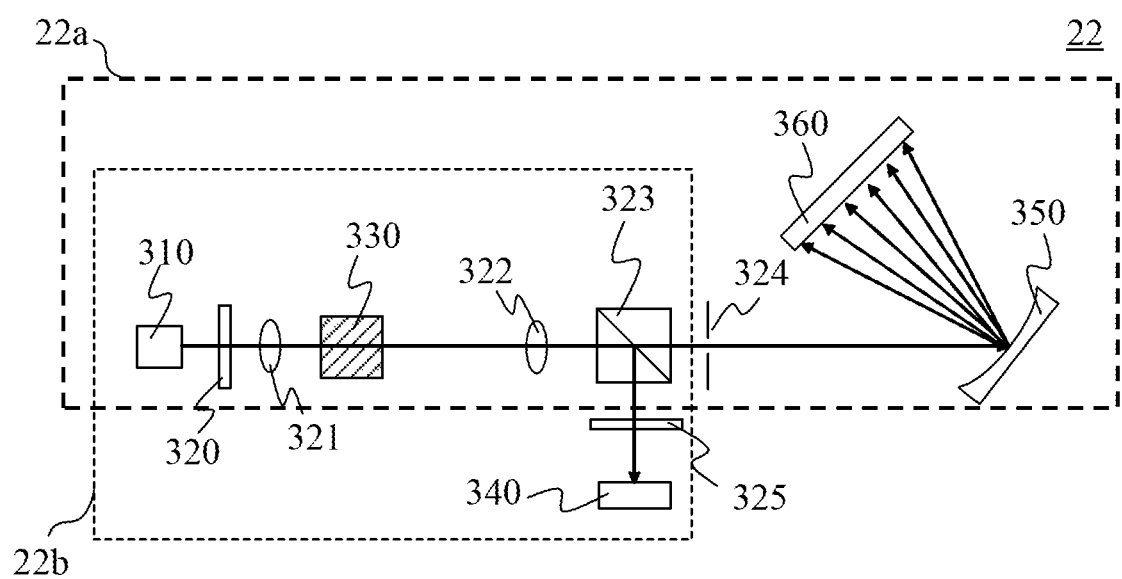
FIG. 12 is a block diagram of a measurement unit according to the third embodiment.

FIG. 12 is a block diagram of the measurement unit 22. The measurement unit 22 includes a transmitted light measurement unit 22a and a scattered light measurement unit 22b. In FIG. 12, the transmitted light measurement unit 22a and the scattered light measurement unit 22b are respectively divided by the light receivers after a beam splitter 323. Light emitted from a white light source (light source) 310 is converted into linear polarization light in an arbitrary direction by a polarization filter 320, passes through the lens 321, and is emitted as parallel light to a reaction vessel 330 containing the mixed liquid.

The light emitted from the reaction vessel 330 is focused by the lens 322 at a slit 324 position. The straight light component transmitted through the beam splitter 323 and the slit 324 is guided to a diffraction grating 350. The light separated into a plurality of wavelengths by the diffraction grating 350 is received by an array sensor (one-dimensional array sensor) 360. Thus, the transmitted light measurement unit 22a measures the wavelength-resolved absorbance of the straight light component having transmitted through the reaction vessel 330.

On the other hand, the scattered light measurement unit 22b measures the intensity of the depolarized component of the light reflected on the beam splitter 323 through the polarization filter 325 set to receive the depolarized light by the detector 340. The scattered light measurement unit 22b may have the same configuration as the automatic analysis apparatus 100 according to the first embodiment or the automatic analysis apparatus 200 according to the second embodiment.

In this embodiment, the transmitted light measurement unit 22a measures the change in color tone (spectrum) caused by the reaction of the mixed solution from the measurement data of the absorbance spectrum, and calculates the concentration and the enzyme activity of a variety of components in the mixed solution. The processor 40 can quantify the concentration of the measuring object in the latex aggregation method based on the measurement result of the transmitted light measurement unit 22a and the scattered light measurement unit 22b. At this time, as described in the first embodiment, depending on the condition of the mixed liquid, one of the measurement data of the depolarization component by the scattered light measurement unit 22b and the absorbance data of straight light of the transmitted light measurement unit 22a is properly selected and analyzed. One of the conditions of the mixed solution is a condition determined under the initial condition of the measurement, such as the size and concentration of the measuring object, the particle size of the reagent (latex particle), the concentration, the type of the reagent, and information of the measurement item. One of other conditions of the mixed liquid is the state of the mixed liquid during the measurement according to the elapsed time after the reaction starts, which is determined based on at least one of the measurement data of the depolarization component by the scattered light measurement part 22b, and the absorbance data of the straight light of the transmitted light measurement part 22a.

Herein, the transmitted light measurement unit 22a and the scattered light measurement unit 22b in the measurement unit 22 may not be arranged at the same position on the disc 21 (the incident optical axis on the reaction vessel 23 is coaxial) as illustrated in FIG. 12. They can be provided at different positions on the disc 21 and separately measured. However, the transmitted light measurement unit 22a and the scattered light measurement unit 22b need to perform the measurement at substantially the same timing (photometry point), and thus the arrangement of the two measurement units is limited. For example, in order to synchronously measure all of the first to thirty-third photometry points illustrated in FIG. 11 between the transmitted light measurement unit 22a and the scattered light measurement unit 22b, the arrangement illustrated in FIGS. 13A-13C is viable.

Figure 13A:
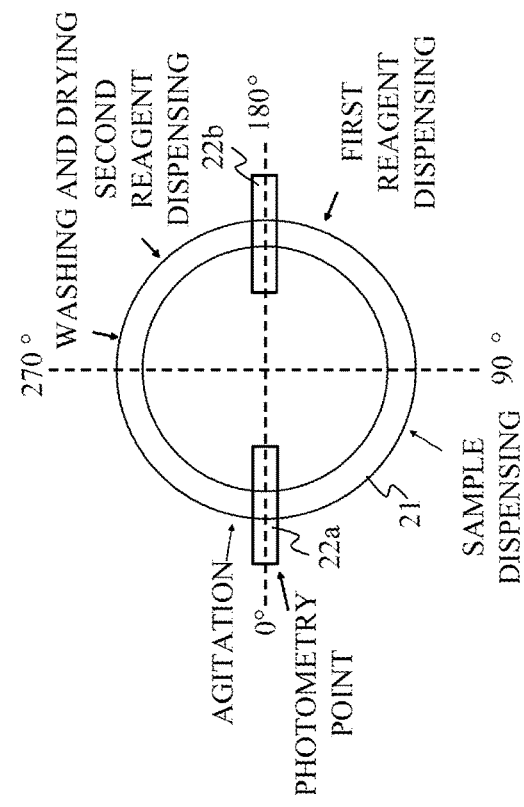
FIGS. 13A to 13C illustrate an arrangement of a transmitted light measurement unit and a scattered light measurement unit according to the third embodiment.
Figure 13B:
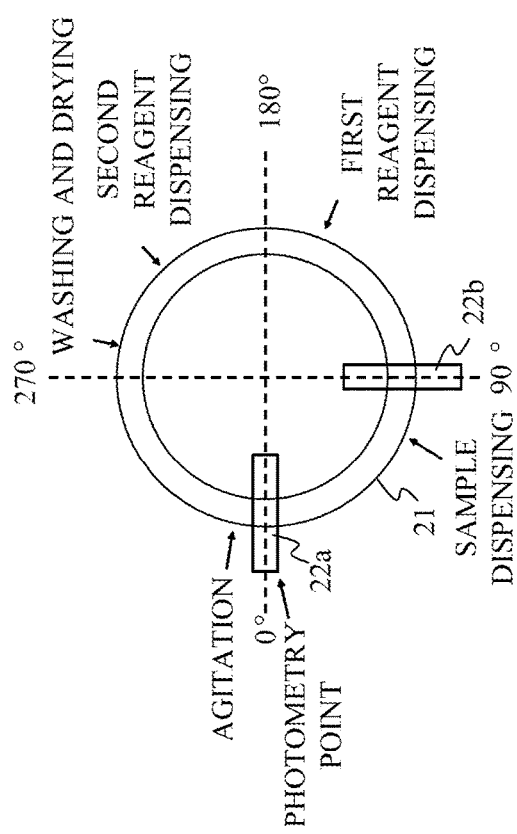
Figure 13C:
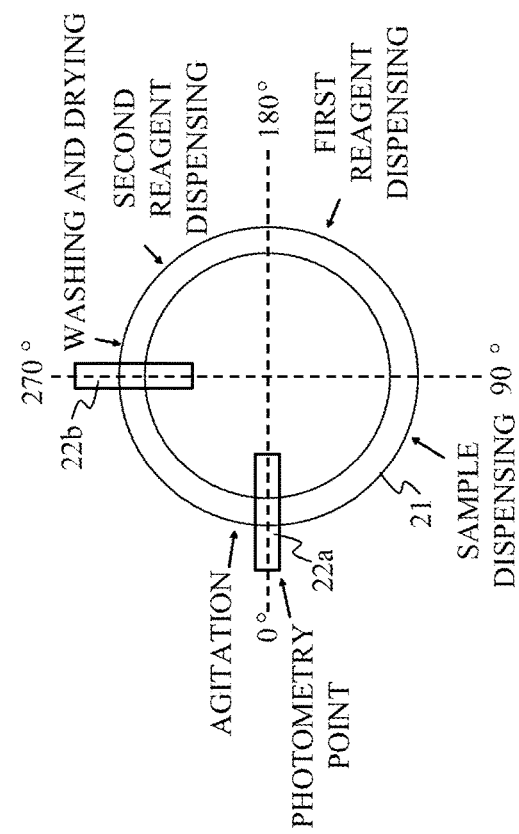

FIGS. 13A to 13C illustrate an arrangement between the transmitted light measurement unit 22a and the scattered light measurement unit 22b. FIGS. 13A to 13C set the photometry point of the transmitted light measurement unit 22a to a reference axis, and arrange the scattered light measurement part 22b at a 90° position (FIG. 13A), a 180° position (FIG. 13B), or a 270° position (FIG. 13C) in the rotational direction of the disc 21. Depending on the angle from the reference axis, although a slight time lag occurs in the measurement between the transmitted light measurement unit 22a and the scattered light measurement unit 22b, all the photometry points can be measured at almost the same timing between them. This time lag can be corrected in the analysis.

Figure 14B:
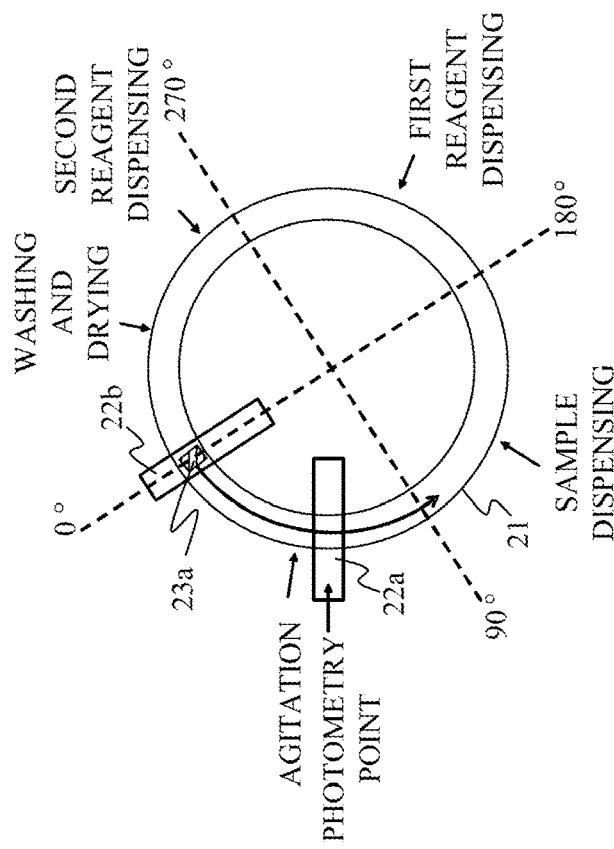
Figure 14A:
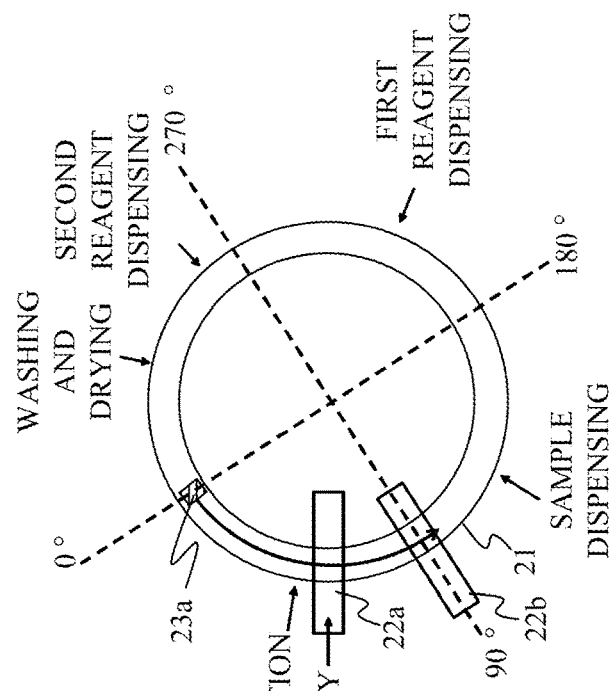

Alternatively, the scattered light measurement unit 22b may measure at the same timing as that of the transmitted light measurement unit 22a on and after the sixteenth measurement point just before the latex aggregation reaction starts. In this case, it is conceivable that the transmitted light measurement unit 22a and the scattered light measurement unit 22b are arranged as illustrated in FIGS. 14A to 14D. FIGS. 14A to 14D illustrate another arrangement of the transmitted light measurement unit and the scattered light measurement unit. FIG. 14A disposes the scattered light measurement unit 22b at the rotation start position of the reaction vessel 23a which measures the sixteenth light measurement point (this is used as a reference axis). Similar to the description with reference to FIGS. 13A to 13C, the scattered light measurement unit 22b may be located at the position of 90° (FIG. 14B), 180° (FIG. 14C), or 270° (FIG. 14D) with respect to the reference axis.

Alternatively, the scattered light measurement unit 22b may start measuring at a timing before the seventeenth photometry point at which the latex aggregation reaction starts, and then may measure in synchronization with the transmitted light measurement unit 22a. The arrangement of the transmitted light measurement unit 22a and the scattered light measurement unit 22b can be determined based on the above description so as to satisfy this condition.

The present invention is applied as one of the measurement functions in an automatic analysis apparatus that automatically dispenses, agitates, measures, sucks, washes, and dries the sample and reagent as in this embodiment, and can provide an automatic analysis apparatus that can analyze the measuring object in combination with a variety of other analyses.

The automatic analysis apparatus (such as the automatic analysis apparatus 100) according to each embodiment includes a reaction vessel (such as the reaction vessel 130), an irradiation unit (such as the polarization filter 120), a measurement unit (such as the polarization filter 160 and detector 170), and the processor (such as the processor 180). The reaction vessel can house a reaction liquid in which the measuring object and the reagent are mixed. The irradiation unit irradiates the reaction vessel with the irradiation light 191 as the predetermined incident light polarization. The measurement unit measures the emitted light 192 emitted from the reaction vessel. The processor processes the signal of the specific polarization component obtained from the measurement unit and analyzes the measuring object. The specific polarization component is determined based on the condition of the reaction liquid 131.

The measurement unit may include a polarization selector (such as the polarization filter 160) configured to select an arbitrary polarization component among the emitted light, and a detector (such as the detector 170) configured to measure the emitted light of an arbitrary polarization component. The processor extracts and processes the signal having a specific polarization component from the arbitrary polarization component based on the condition of the reaction liquid. The incident light polarization may be a linear polarization, and the arbitrary polarization component may include at least one of a perpendicular component perpendicular to the incident light polarization and a parallel component parallel to the incident light polarization.

The processor may process the signal based on at least one of the signal intensity and the time variation of the signal. The processor may compare a first signal as a signal when the reaction starts for mixing the measuring object and the reagent, with a second signal as a signal an arbitrary time after the reaction starts, and analyzes the measuring object based on a change (change amount) of the second signal relative to the first signal.

The condition of the reaction liquid may include an initial condition of the reaction liquid. The initial condition of the reaction liquid is determined based on at least one of the size and concentration of the measuring object. The initial condition of the reaction liquid is determined based on at least one of the size and concentration of the reagent, the type of the reagent, and the measurement item of the test.

The conditions of the reaction liquid may include the condition during the reaction of the reaction liquid. The specific polarization component may be determined such that the signal change increases over time after the reaction of the reaction liquid starts.

The measurement unit may control the angular range of the scattering angle and measure the emitted light where the scattering angle is set to an angle at which the emitted light exits from the reaction vessel relative to an incident axis when the irradiated light enters the reaction vessel. The measurement unit may set the angular range based on at least one of the condition of the reaction liquid, the polarization component of the emitted light measured by the measurement unit, the signal intensity, and the time variation of the signal. The measurement unit limits the angle range to a predetermined angle range (angle near the incident axis), and measures at least one of a perpendicular component perpendicular to the incident light polarization and a parallel component parallel to the incident light polarization. The measurement unit may include a plurality of polarization selectors (such as polarization filters 160 and 161) configured to select an arbitrary polarization component of the emitted light, and the plurality of polarization selectors correspond to mutually different scattering angles.

The measurement unit includes an array sensor (two-dimensional array sensor). The measurement unit may measure the emitted light of the perpendicular component perpendicular to the incident light polarization and acquire two-dimensional intensity distribution data of the perpendicular component, and the processor may process the two-dimensional intensity distribution data. The processor may generate measurement data including a plurality of signals measured at a plurality of pixel positions of the array sensor corresponding to the same (approximately the same) scattering angle, and process the measurement data after removing a signal exceeding a threshold set for the measurement data from the plurality of signals. The measuring unit may measure an arbitrary polarization component of the emitted light in pixel unit in the array sensor, change the signal output so that the signal corresponding to the arbitrary polarization component does not saturate, and perform a measurement.

The irradiation unit may temporally modulate the irradiation light at a predetermined modulation frequency, and lock-in detect the irradiation light using a reference signal having the predetermined modulation frequency. The incident light polarization may be linear polarization, and the measurement unit may measure the emitted light of each of polarization components of 0°, 45°, 90°, and 135° relative to the linear polarization, and the processor may determine the linear polarization degree from the signal, and processes based on the linear polarization degree. The processor may calculate an autocorrelation function of the signal, evaluate a relaxation rate of the autocorrelation function, and analyze a time variation of the signal. The processor may analyze a temporal variation of the signal having a perpendicular component perpendicular to the incident light polarization. The measurement unit may measure the emitted light of the perpendicular component perpendicular to the incident light polarization and the parallel component parallel to the incident light polarization. The processor may compare the relaxation time calculated from the signal having the perpendicular component with the relaxation time calculated from the signal having the parallel component, and analyze the temporal variation of the signal.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The automatic analysis apparatus according to each embodiment analyzes the component of a test sample using a latex aggregation reaction, has a simple configuration, and analyzes a reaction liquid with a high sensitivity from a low concentration to a high concentration. Therefore, each embodiment can provide an automatic analysis apparatus, an automatic analysis method, and a program, each of which is highly sensitive and has a simple configuration.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-148340 filed on Aug. 7, 2018, which is hereby incorporated by reference herein in its entirety.

What is claimed is:

1. An automatic analysis apparatus comprising:
a reaction vessel configured to contain a reaction liquid in which a measuring object and a reagent are mixed with each other;
an irradiation unit configured to irradiate the reaction vessel with irradiation light as predetermined incident light polarization;
a measurement unit configured to measure light emitted from the reaction vessel; and
a processor configured to process a signal having a specific polarization component obtained from the measurement unit and to analyze the measuring object,
wherein the specific polarization component is determined based on the condition of the reaction liquid.

2. The automatic analysis apparatus according to claim 1, wherein the measurement unit includes a polarization selector configured to select an arbitrary polarization component in the emitted light, and a detector configured to measure the emitted light having an arbitrary polarization component, and
wherein the processor extracts and processes the signal having the specific polarization component from the arbitrary polarization component based on the condition of the reaction liquid.

3. The automatic analysis apparatus according to claim 2, wherein the incident light polarization is a linear polarization, and
wherein the arbitrary polarization component includes at least one of a perpendicular component perpendicular to the incident light polarization and a parallel component parallel to the incident light polarization.

4. The automatic analysis apparatus according to claim 1, wherein the processor selects a polarization component measured by the measurement units based on the condition of the reaction liquid, and determines an aggregation degree of the reaction liquid.

5. The automatic analysis apparatus according to claim 1, wherein the processor processes the signal based on at least one of an intensity of the signal or a time variation of the signal.

6. The automatic analysis apparatus according to claim 1, wherein the processor compares a first signal as the signal when a reaction starts for mixing the measuring object and the reagent, and a second signal as the signal an arbitrary time after the reaction starts, and
wherein the processor analyzes the measuring object based on a change in the second signal relative to the first signal.

7. The automatic analysis apparatus according to claim 1, wherein the condition of the reaction liquid includes an initial condition of the reaction liquid.

8. The automatic analysis apparatus according to claim 7, wherein the initial condition of the reaction liquid is determined based on at least one of a size and a concentration of the measuring object.

9. The automatic analysis apparatus according to claim 7, wherein the initial condition of the reaction liquid is determined based on at least one of a size and a concentration of the reagent, a type of the reagent, and a measurement item of a test.

10. The automatic analysis apparatus according to claim 1, wherein the condition of the reaction liquid includes a condition during a reaction of the reaction liquid.

11. The automatic analysis apparatus according to claim 10, wherein the specific polarization component is determined such that a change in the signal increases over time after the reaction of the reaction liquid starts.

12. The automatic analysis apparatus according to claim 1, wherein the measurement unit controls an angular range of the scattering angle and measures the emitted light, where the scattering angle is an angle at which the emitted light exits from the reaction vessel relative to an incident axis when the irradiation light enters the reaction vessel.

13. The automatic analysis apparatus according to claim 12, wherein the measurement unit sets the angular range based on at least one of the condition of the reaction liquid, a polarization component of the emitted light measured by the measurement unit, the intensity of the signal, and the time variation of the signal.

14. The automatic analysis apparatus according to claim 12, wherein the measurement unit limits the angle range to a predetermined angle range, and measures the emitted light of at least one of a perpendicular component perpendicular to the incident light polarization and a parallel component parallel to the incident light polarization.

15. The automatic analysis apparatus according to claim 12, wherein the measurement unit includes a plurality of polarization selectors configured to select an arbitrary polarization component in the emitted light, and
wherein the plurality of polarization selectors are disposed at positions corresponding to scattering angles different from one another.

16. The automatic analysis apparatus according to claim 12, wherein the measurement unit includes an array sensor.

17. The automatic analysis apparatus according to claim 16, wherein the measurement unit measures the emitted light of a polarization component perpendicular to a polarization direction of the incident light polarization and obtains two-dimensional intensity distribution data of the perpendicular polarization component, and
wherein the processor processes the two-dimensional intensity distribution data.

18. The automatic analysis apparatus according to claim 16, wherein the processor generates measurement data including a plurality of signals respectively measured at a plurality of pixel positions of the array sensor corresponding to the same scattering angle, and performs processing after removing a signal exceeding a threshold set for the measurement data from the plurality of signals.

19. The automatic analysis apparatus according to claim 16, wherein the measurement unit measures an arbitrary polarization component of the emitted light in a pixel unit of the array sensor, and performs a measurement by changing an output of the signal so that the signal corresponding to the arbitrary polarization component does not saturate.

20. The automatic analysis apparatus according to claim 1, wherein the irradiation unit temporally modulates the irradiation light at a predetermined modulation frequency, and lock-in detects the irradiation light using a reference signal of the predetermined modulation frequency.

21. The automatic analysis apparatus according to claim 1, wherein the incident light polarization is a linear polarization,
wherein the measurement unit measures the emitted light of polarization components of 0°, 45°, 90°, and 135° relative to the linear polarization, and
wherein the processor calculates a linear polarization degree from the signal and performs processing based on the linear polarization degree.

22. The automatic analysis apparatus according to claim 1, wherein the processor calculates an autocorrelation function of the signal, evaluates a relaxation rate of the autocorrelation function, and analyzes a time variation of the signal.

23. The automatic analysis apparatus according to claim 1, wherein the processor analyzes a temporal variation of the signal having a polarization component perpendicular to the incident light polarization.

24. The automatic analysis apparatus according to claim 1, wherein the measurement unit measures a two-dimensional intensity distribution of a polarization component perpendicular to the polarization direction of the incident light polarization, and a temporal variation of the signal corresponding to the two-dimensional intensity distribution, and
wherein the processor calculates a two-dimensional relaxation rate distribution relating to the relaxation rate of the autocorrelation function of the signal using the time variation, and analyzes the measuring object using the two-dimensional intensity distribution and the two-dimensional relaxation rate distribution.

25. The automatic analysis apparatus according to claim 1, wherein the measurement unit measures the emitted light of a perpendicular component perpendicular to the incident light polarization and a parallel component parallel to the incident light polarization, and
wherein the processor analyzes the time variation of the signal by comparing the relaxation time calculated from the signal having the perpendicular component with the relaxation time calculated from the signal having the parallel component.

26. An automatic analysis method comprising the steps of:
irradiating a reaction vessel configured to contain a reaction liquid in which a measuring object and a reagent are mixed with each other, with irradiation light as predetermined incident light polarization;
measuring light emitted from the reaction vessel; and
processing a signal having a specific polarization component obtained from the measurement unit and to analyze the measuring object,
wherein the specific polarization component is determined based on the condition of the reaction liquid.

27. A non-transitory computer-readable storage medium storing a program that causes a computer to execute the automatic analysis method,
wherein the automatic analysis method includes the steps of:
irradiating a reaction vessel configured to contain a reaction liquid in which a measuring object and a reagent are mixed with each other, with irradiation light as predetermined incident light polarization;
measuring light emitted from the reaction vessel; and
processing a signal having a specific polarization component obtained from the measurement unit and to analyze the measuring object,
wherein the specific polarization component is determined based on the condition of the reaction liquid.

* * * * *